United States Patent [19]

Shalhoob et al.

[11] Patent Number: 4,537,181
[45] Date of Patent: Aug. 27, 1985

[54] HYDROMAGNETIC APPARATUS FOR NON-SURGICAL IN VIVO REMOVAL OF CALCIUM DEPOSITS

[75] Inventors: William N. Shalhoob, Santa Ynez; Alfred F. Kaspaul, Malibu, both of Calif.

[73] Assignee: Hydromagnetics, Inc., Solvang, Calif.

[21] Appl. No.: 966,630

[22] Filed: Dec. 5, 1978

[51] Int. Cl.$^3$ .............................................. A61N 1/42
[52] U.S. Cl. .................................................... 128/1.3
[58] Field of Search ................................... 128/1.3–1.5

[56] References Cited

U.S. PATENT DOCUMENTS

| 1,120,964 | 12/1914 | Neel | 128/1.5 |
| 1,375,050 | 4/1921 | Krauer | 128/1.5 |
| 3,467,076 | 9/1969 | Frisch et al. | 128/1.3 |
| 3,658,051 | 4/1972 | MacLean | 128/1.5 |
| 3,890,953 | 6/1975 | Kraus et al. | |
| 4,177,796 | 12/1979 | Franco-Vila | |

FOREIGN PATENT DOCUMENTS

| 2506227 | 8/1976 | Fed. Rep. of Germany | 128/1.3 |
| 305664 | 2/1933 | Italy | 128/1.3 |

OTHER PUBLICATIONS

Bachelet, E., "An Address to the Medical Profession", 1906.
Alexander, H. S., Am. Journ. of Med. Electronics, Jul.–Sep., 1962, pp. 181–187.

Primary Examiner—Lee S. Cohen
Attorney, Agent, or Firm—Kenneth E. Darnell

[57] ABSTRACT

A method and apparatus for removal of unwanted calcium from living organisms, particularly man, the invention provides non-invasive treatment modes for conditions such as arthritis and the like by subjection of the affected portion of the body to rotating magnetic fields. In particularly, magnetic members supported on a rotary plate and positioned thereon in an alternating polarity arrangement are caused to rotate at a desired angular velocity, the portion of the body which is subjected to the magnetic field being spaced from the rotating magnetic members at a desired distance. A magnetic field intensity of 50 gauss, such as at a distance of 12 inches, has been found to be effective at a rotational speed of 55 rpm, treatments preferably occurring periodically for a duration of from several minutes to approximately an hour at spaced temporal intervals over a several month period. The present treatment modes yield relief from discomfort and cause the body to eliminate excess calcium.

4 Claims, 6 Drawing Figures

HYDROMAGNETIC APPARATUS FOR NON-SURGICAL IN VIVO REMOVAL OF CALCIUM DEPOSITS

BACKGROUND OF THE INVENTION

1. Field of the Invention

The invention relates generally to non-invasive therapeutic modes of treatment of arthritis and similar systemic disease syndromes and particularly to methods and apparatus for treating such disease syndromes magnetically.

2. Description of the Prior Art

Treatment of the human body with magnetic fields has previously been known in the art, prior treatments ranging from the wearing of magnetic members on portions of the body to the use of high intensity pulsed magnetic fields which could cause dissociation of body fluids. As examples, Nakayama, in U.S. Pat. No. 3,921,620, describes the interaction of flowing, conductive fluids with stationary magnetic fields in the treatment of the body. Kraus et al, in U.S. Pat. No. 3,890,953 arranges stationary magnetic fields in a parallel orientation with respect to body fibers, bone structures and the like. MacLean, in U.S. Pat. No. 3,658,051, uses pulsed magnetic fields having an intensity on the order to 2,000 gauss. Elmi, in U.S. Pat. No. 3,337,776, discusses the interaction of flowing, conductive liquids with magnetic fields. Neel, in U.S. Pat. No. 1,120,964, also describes body treatment modes using magnetic fields. The prior art does not, however, provide treatment modes and apparatus for effecting such treatment modes which subject the body or affected portions thereof to rotating magnetic fields of particular field intensity in order to relieve arthritis and similar disease syndromes which result from excessive calcium deposits in the body.

SUMMARY OF THE INVENTION

The invention provides methods and apparatus for treatment of arthritis and similar disease syndromes by subjection of the body or affected portions thereof to rotating magnetic fields having intensities sufficient to prevent calcium deposition from the electrolyte flowing within the body, that is, blood, the invention acting further to dissolve calcium deposits present in the body. The present invention particularly provides treatment modalities for conditions such as rheumatoid arthritis, the treatments providing further a systemic benefit additional to the symptomatic relief of relatively localized arthritic discomfort. Affected portions of the body are subjected to a rotating magnetic field, preferably to oppositely disposed counter-rotating magnetic fields, which produce a desired magnetic field intensity at the affected body portion. Magnetic fields suitable for practice of the invention are preferably induced by ceramic "donut" magnets disposed in a desired relation to each other on a support plate which can be rotated at desired rotational speeds by motor. Arcuate magnetic segments can also be disposed on a rotatable support plate to form a circular magnetic structure, outermost portions of the alternate magnetic segments having opposite polarities.

The imposition of a 50 gauss magnetic field at a distance of approximately 12 inches from an affected body portion is typically adequate for treatment according to the invention, the affected body portion typically being subjected to such treatment for approximately 30 minutes over a period of time, such as approximately 3 times per week for 6 weeks or longer. Due to the recurrance of calcium deposits within the body, the invention does not provide a "cure" per se but does provide a therapeutic treatment modality which provides symptomatic relief and systemic benefit.

Accordingly, it is an object of the present invention to provide methods and apparatus for treatment of arthritis and similar disease syndromes which at least in part are caused by excessive deposits of calcium in the body.

It is another object of the present invention to provide methods and apparatus for subjecting the body or portions thereof to rotating magnetic fields of desired intensity for periods of time sufficient to cause dissolution of excessive calcium deposits in the body, thereby allowing the body to eliminate such excess calcium.

Further objects and advantages of the invention will become more readily apparent in light of the following detailed description of the prefered embodiments of the invention.

DESCRIPTION OF THE PREFERRED EMBODIMENTS

Figure 1:
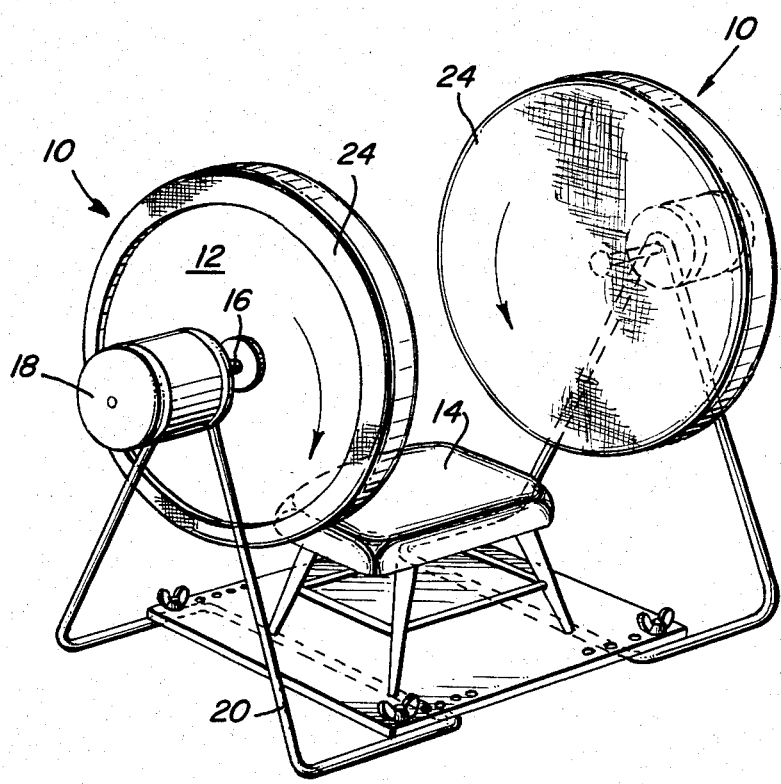
FIG. 1 is an elevational view of a treatment apparatus according to the invention.
Figure 2:
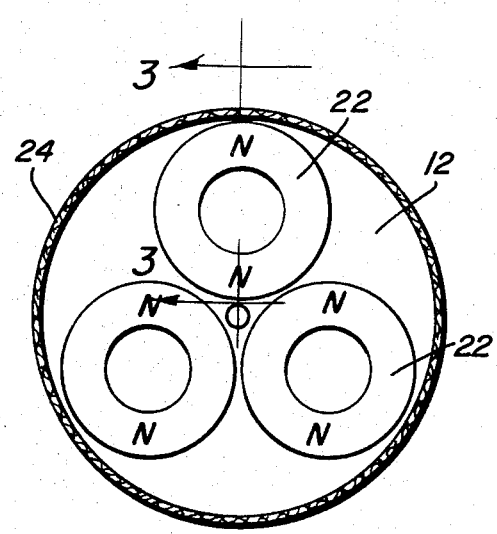
FIG. 2 is a front elevational view of a portion of the apparatus of FIG. 1 taken generally along lines 2—2 of FIG. 1.
Figure 3:
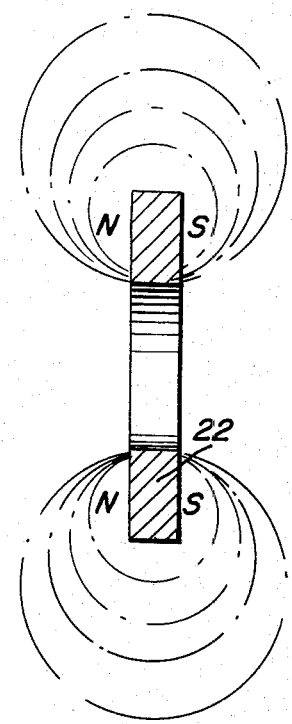
FIG. 3 is a sectional view taken along lines 3—3 of FIG. 2.

Referring now to the drawings and particularly to FIGS. 1-3, a first embodiment of the invention is shown to comprise a pair of spaced opposing rotary magnetic assemblies 10, the magnetic assemblies 10 being essentially identical. Accordingly, a description of one of the assemblies 10 will suffice for both of said assemblies. It is to be understood that each assembly 10 has a magnet-bearing rotary plate 12, the plates 12 being disposed on opposite sides of a portion of the body which is to be subjected to a magnetic field according to the invention. A desired magnetic field intensity is thus produced by the structure of the invention at a desired location between the rotary plates 12. It is further to be understood that the invention could be practiced with only one of the assemblies 10 or with a larger number of such assemblies as desired. In a typical treatment situation, a seat 14 is provided between the plates 12 and substantially equidistant therefrom a user resting on the seat and positioning an affected portion of the body substantially medially between said plates 12. The plate 12 of each assembly 10 is centrally supported by a rotary shaft 16 driven by motor 18, the motor 18 being supported by a suitable support stand 20.

As further can be seen in FIGS. 2 and 3, each of the plates 12 mount "donut" magnetic members 22 in equidistantly spaced relation about the center of said plate. The magnetic members are preferably ceramic magnets having approximately a 6 inch outer diameter, a 3 inch inner diameter and a thickness of 0.75 inch. The magnets are chosen to produce a desired field intensity at a given distance from the plate 12, the field intensity being chosen in order to maximize a desired treatment effect. The magnetic members 22 are preferably chosen to produce a magnetic field intensity of approximately 50 gauss at a distance of 12 inches from the surface of the plate 12. The magnetic members 22 are preferably disposed on the plate 12 such that the "north" poles are disposed outwardly of the plate 12, the "south" poles being essentially disposed in contiguous relation to the plate 12. Magnetic members 22 so configured and so disposed on the plate 12 operate to provide a desired magnetic field intensity, it being understood, however, that other configurations capable of providing suitable magnetic field intensities according to the teachings hereindisclosed are also contemplated by the invention. As further seen in FIG. 1, a fabric cover 24 can be provided over the plate 12 and magnetic members 22.

The motor 18 can be either a variable speed or fixed speed prime mover preferably driven electrically. A typically suitable rate of rotation of the plate 12 is approximately 55 rmp. However, it is to be understood that the plates 12 can be driven at lesser or greater angular rates without departing from the scope of the invention.

Figure 4:
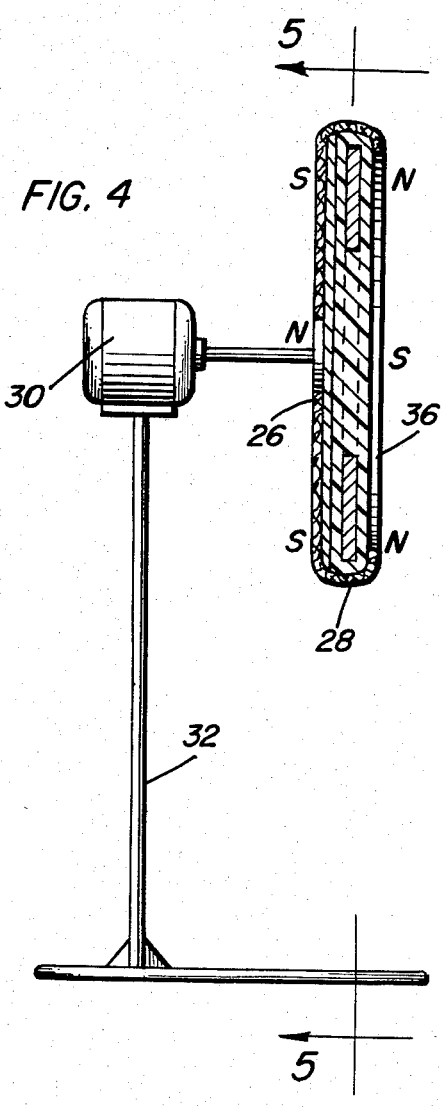
FIG. 4 is an elevational view of a treatment apparatus comprising a second embodiment of the invention.
Figure 5:
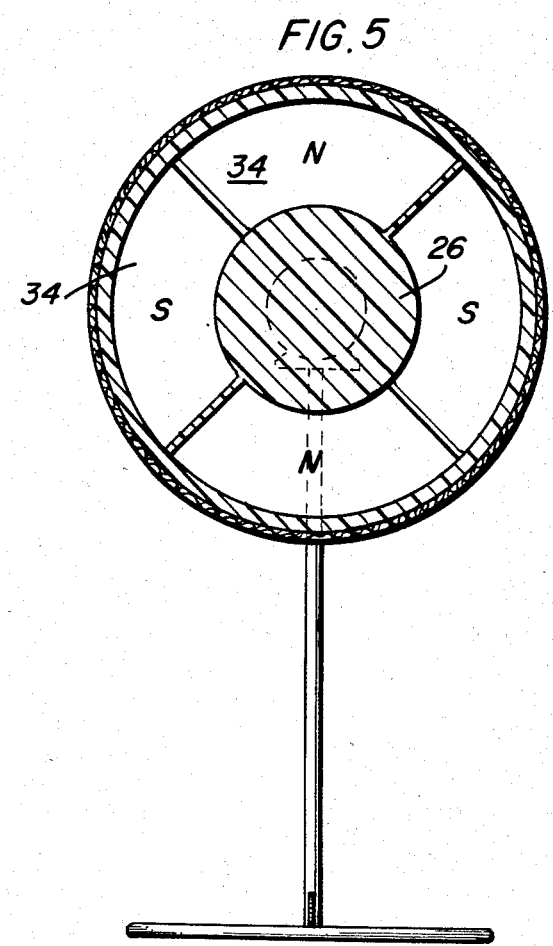
FIG. 5 is a front elevational view of a portion of the apparatus of FIG. 4 taken generally along lines 5—5 of FIG. 4; and, FIG. 6 is a sectional view taken along lines 6—6 of FIG. 5.
Figure 6:
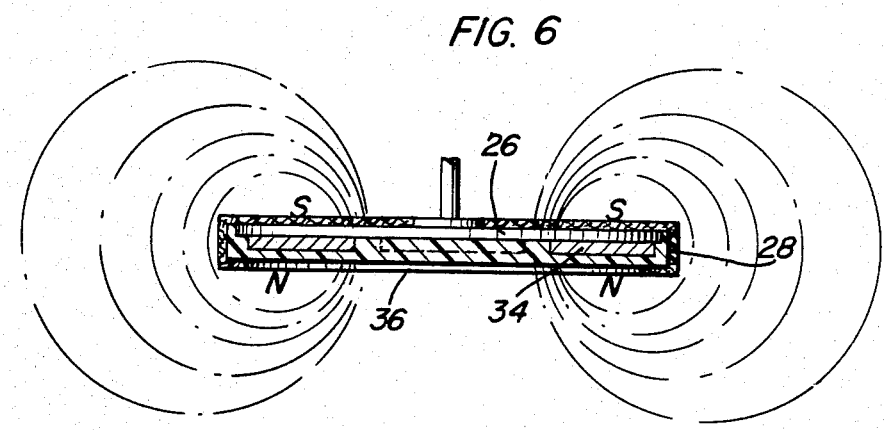

Referring now to FIGS. 4–6, a second embodiment of the invention which can be readily substituted into the treatment situation shown generally in FIG. 1 is seen to comprise a rotary plate 26 which is preferably formed of aluminum and which has an annular perimetric flange disposed about the outer periphery thereof. The plate 28 is rotated by a motor 30 in a manner essentially identical to that described relative to the plate 12 of FIG. 1. The motor 30 is, of course, suitably supported by support stand 32 in an obvious fashion.

The plate 26 supports magnetic segments 34, the segments 34 essentially comprising arcuate chord-like members which essentially cooperate to form an annular ring on the surface of the plate 26. An even number of the segments 34 can be provided to form the aforesaid annular ring. As particularly seen in FIG. 5, alternate segments 34 have outer surfaces of opposite polarities, a segment 34 with the "south" pole disposed outwardly having segments 34 adjacent thereto with the "north" poles thereof disposed outwardly. The magnetic segments 34 can be encased on the plate 26 by means of a cover 36 which may be formed of glass or plastic material.

The treatment principle underlying the present treatment modalities are essentially hydromagnetic in nature. It is known that an electric field vector results when a conductive liquid enters a homogeneous magnetic field which has a magnetic field vector (or vector component) disposed perpendicularly to the direction of the flowing water. The resulting electric field vector is perpendicular to both the magnetic field vector and the direction of flow of the liquid. An electrical potential is thus generated. It is also known that a magnetic field may be moved relatively to a body of conductive liquid in order to produce essentially the same physical situation. According to the teachings of the present invention, the conductive body liquid known as blood is caused to flow through an essentially homogeneous magnetic field in order to produce a desired result. More particularly, when the conductive liquid (blood) enters the rotating magnetic field produced by the structure of the invention, the magnetic field vector being preferably disposed perpendicularly to the direction of the flowing liquid, an electric field vector results which is perpendicular to both the magnetic field vector and the direction of the flow of the liquid. An electrical potential is thus generated which may be measured by inserting appropriate electrodes (not shown) into the flowing liquid, it also being possible to calculate the absolute value of the electrical potential according to the following relation:

$$E_0 = \bar{v} \cdot b \cdot B \text{ (in volts)}$$

where:

B is a given magnetic field with an electrode spacing b, the output voltage $E_0$ increasing linearly with the average velocity of the conductive liquid $\bar{v}$. The combined influence of the magnetic and electric fields, as well as resulting electrical currents, leads to complex interactions with dissolved ions in the liquid. In the present system which involves a flow of the conductive liquid blood and rotation of the magnetic field, these interactions act to maintain calcium in solution in the blood and further to dissolve calcium into the blood for elimination from the body. Thus, the present treatment provides symptomatic relief for conditions such as arthritis and the like, a systemic benefit being also provided according to the subjective evidence provided by individuals who have been subjected to such treatment.

As an example of an effective treatment modality according to the invention, a patient suffering with rheumatoid arthritis over a period of 9 years was treated with the structure of FIG. 1. The patient showed classic rheumatoid arthritis symptoms over the period of time during which the disease developed, that is, pain in first one joint and then subsequently in a number of parts of the body. Although dietary measures act to maintain a certain control of the symptoms of the disease, pain is experienced in the patient from time to time, especially during bad weather and during periods of stress. The patient was treated with the apparatus of FIG. 1 in a manner such that the magnetic members 22 on each assembly 10 produced a field of approximately 50 gauss at approximately a 12 inch distance from each of said plates 12. The plates 12 were spaced approximately 4 feet apart, that is, sufficiently to space the patient approximately 12 inches from each of the plates 12. The plates 12 were counter-rotated relative to each other at an angular velocity of approximately 55 rpm's. The patient was treated approximately 3 times per week over a period of 6 weeks, the first treatment lasting for 4 minutes with each successive treatment being increased by 2 minutes until the treatment period reached one-half hour per treatment. The treatments were particularly directed to the right thumb and right knee of the patient, the two areas which were most painful during this period of time, the right thumb and right knee being appropriately positioned between the counter-rotating plates 12. After 4 treatment sessions, the subjectively realized discomfort in both the knee and thumb had considerably lessened and the patient had regained normal mobility in the thumb, all three joints of which had been swollen and stiff prior to treatment. The swelling in two of the joints disappeared entirely during the treatment series, the patient being able to use the thumb in a relatively normal manner. The patient further reported subjectively that the usual symptoms of arthritis apparently disappeared in other portions of the body except for occasional slight discomfort, such a condition being unusual due to the fact that the patient was undergoing considerable stress and was subjected to weather conditions which normally would cause aggravation of the arthritic conditions. The patient did not use any chemical or other treatment during this period of time. Urine and blood analysis indicated that the patient's body was disposing of a substantially greater amount of calcium than was normally eliminated.

It is therefore to be seen that treatment of rheumatoid arthritis and similar conditions can be accomplished through the practice of the present invention. However, it is to be understood that the invention is not to be limited to the methods and structure explicitly described hereinabove, the scope of the invention being only limited by the scope of the appended claims.

What is claimed:

1. Apparatus for treatment of arthritic conditions of the body, comprising:

magnetic means for producing a magnetic field of an effetive field intensity, the magnetic means comprising a support plate and a plurality of annular magnetic segments disposed on one face of the support plate, the polarity of outer portions of each segment being opposite to the polarity of outer portions of adjacent segments; and means for rotating the magnetic means at a desired rotational speed.

2. The apparatus of claim 1 wherein the magnetic means comprise at least two spaced and oppositely facing rotary support plates having magnet members disposed thereon, the plates being adapted to be disposed on opposite sides of an arthritically-affected body portion which is to be treated.

3. The apparatus of claim 1 wherein the magnetic means produce a magnetic field intensity of approximately 50 gauss at the body portion which is to be treated.

4. The apparatus of claim 1 wherein the magnetic segments are disposed in spaced relation on the support plate and have like poles facing in like directions, said poles being adapted to be disposed in oppositely facing relation to an arthritic-affected body portion which is to be treated.

* * * * *